United States Patent [19]

DeLuca et al.

[11] Patent Number: 4,790,818

[45] Date of Patent: Dec. 13, 1988

[54] METHOD FOR CLEARING EPIGLOTTAL PASSAGES

[76] Inventors: James T. DeLuca, 15 Wendover Rd., Forest Hills Gardens, N.Y. 11375; Michael Fasano, 29 Henni Ct., Syosset, N.Y. 11791

[21] Appl. No.: 720,019

[22] Filed: Apr. 4, 1985

Related U.S. Application Data

[63] Continuation-in-part of Ser. No. 486,217, Aug. 18, 1983, abandoned.

[51] Int. Cl.⁴ .............................................. A61M 31/00
[52] U.S. Cl. ...................................... 604/54; 604/118; 128/204.25; 128/205.19
[58] Field of Search ....................... 128/204.25, 205.19; 604/140, 149, 150, 117, 118, 119, 54; 433/91, 95, 96

[56] References Cited

U.S. PATENT DOCUMENTS

| | | | |
|---|---|---|---|
| 1,843,169 | 2/1932 | McKisson | 604/902 |
| 2,575,513 | 11/1951 | Fox | 604/149 |
| 3,499,393 | 3/1970 | Bent | 604/902 |
| 3,628,532 | 12/1971 | Magrath | 128/205.24 |
| 3,665,919 | 5/1972 | Laerdal | 604/149 |
| 3,939,830 | 2/1976 | da Costa | 604/77 |
| 4,253,831 | 3/1981 | Eaton | 433/91 |
| 4,300,550 | 11/1981 | Gandi et al. | 604/35 |
| 4,451,257 | 5/1984 | Atchley | 604/902 |

*Primary Examiner*—C. Fred Rosenbaum
*Assistant Examiner*—J. L. Kruter
*Attorney, Agent, or Firm*—Charles E. Temko

[57] ABSTRACT

A method of removing obstructions lodged in the pharnyx and/or larnyx of a victim, including the steps of providing a suction device incorporating a rigid hollow tongue depressor having suction means at a free end thereof; inserting said tongue depressor to a point wherein the free end is adjacent an area in which the obstruction is located; applying suction to the free end to dislodge the obstruction and retain it on the free end, and maintaining the suction while withdrawing the tongue depressor and the obstruction engaged thereon.

1 Claim, 1 Drawing Sheet

U.S. Patent
Dec. 13, 1988
4,790,818
FIG. 1.
FIG. 2.
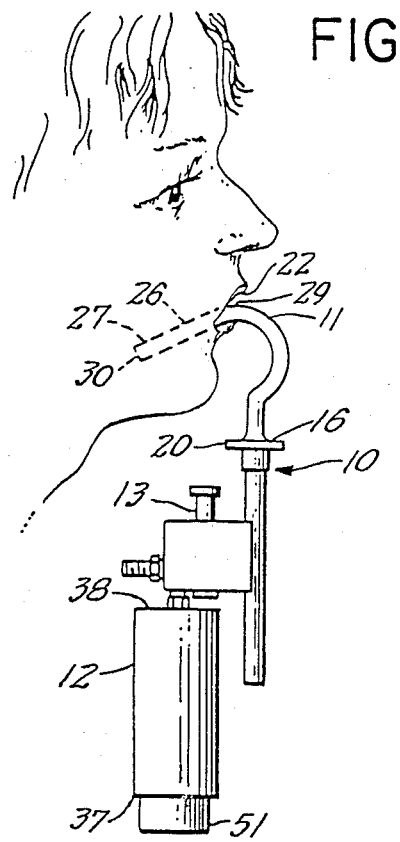
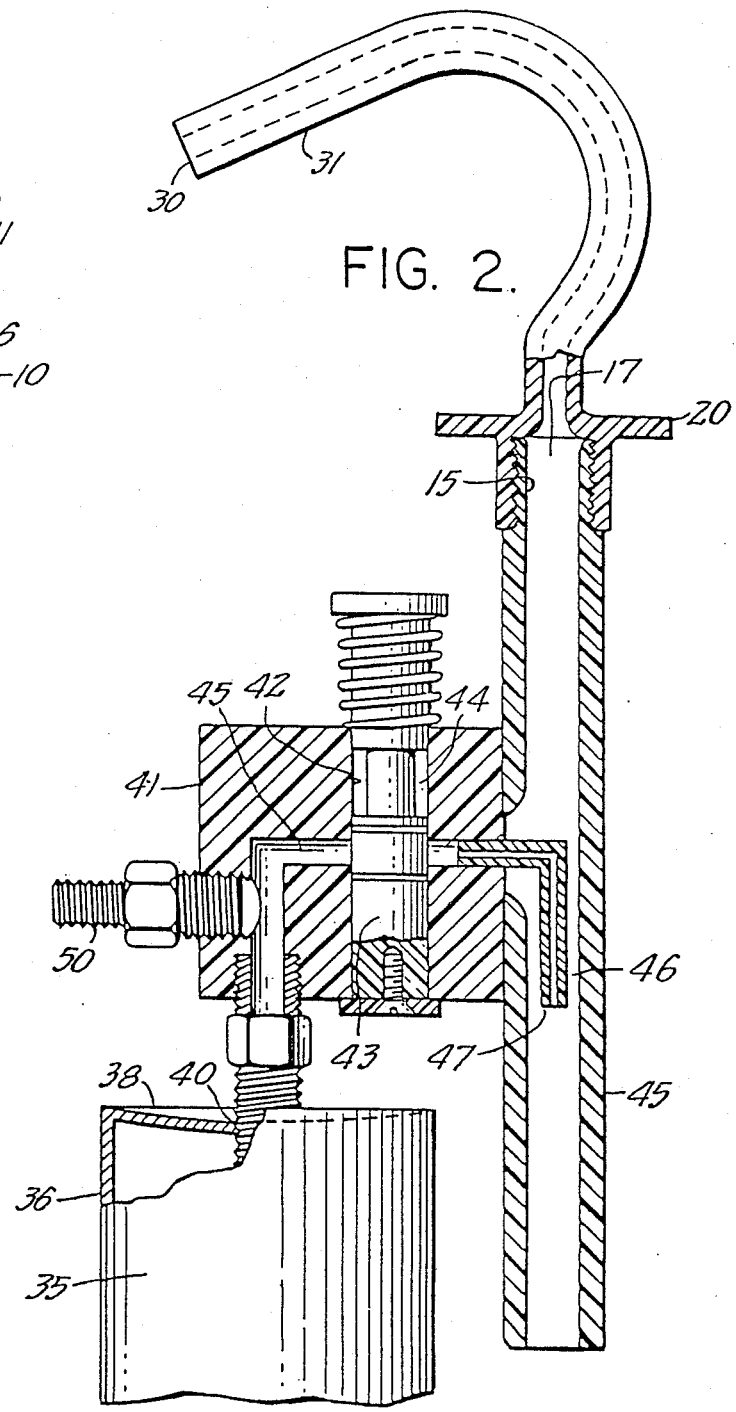

METHOD FOR CLEARING EPIGLOTTAL PASSAGES

RELATED INVENTION

This application is a continuation-in-part of our copending application Ser. No. 06/486,217 filed Aug. 18, 1983 now abandoned under the title DEVICE FOR CLEARING EPIGLOTTAL PASSAGES.

BACKGROUND OF THE INVENTION

This invention relates generally to the field of surgical instrumentation, and more particularly to an improved device for removing obstructions, usually large particles of food, which have accidentally become lodged in the pharynx and trachea to cause choking. While various first aid procedures are known to relieve the victim, such procedures require substantial skills which are not always available when an emergency situation occurs. Instruments which require direct engagement with the particle can be used only by professional persons, and back slapping is not always effective.

It is known in the art to provide jet suction devices, as exemplified by the McGrath U.S. Pat. No. 3,628,532 for the removal of fluids and semifluids from the lungs and breathing passages of animals. The advantage of using jet type suction is that it avoids creating excessive negative pressures within the body of the animal, without the necessity of providing relief valves. Such devices, while useful, do not contemplate the engagement of solid objects which are not capable of being sucked down a tube outwardly of the mouth of the animal.

SUMMARY OF THE INVENTION

Briefly stated, the invention contemplates the provision of an improved vacuum device, including a hollow tongue depressor element having a free open end which is positioned in the throat of the victim. With the application of a vacuum to the depressor element, the lodged object is sucked from its position and either falls free for swallowing by the victim, or, preferably the object is retrieved at the end of the tongue depressor element and held under vacuum as it is removed through the mouth of the user. The vacuum source is most conveniently a canister having a manually actuated valve connected to the tongue depressor element, the canister being under high pressure and discharging a large quantity of gas through a small jet orifice in a tube to create a suction in the tongue depressor element. The nostrils of the victim need not be covered, and thus there is no interference with the normal breathing of the user.

BRIEF DESCRIPTION OF THE DRAWING

In the drawing, to which reference will be made in the specification, similar reference characters have been employed to designate corresponding parts throughout the several views.

FIG. 1 is a side elevational view of an embodiment of the invention.

FIG. 2 is a fragmentary cross-sectional view thereof.

DETAILED DESCRIPTION OF THE DISCLOSED EMBODIMENT

In accordance with the invention, the device, generally indicated by reference character 10, comprises broadly: a tongue depressor element 11, a vacuum source element 12, and a manually actuated valve means 13.

The tongue depressor element 11 is most suitably formed as a synthetic resinous molding operation, and includes a base member 16 forming a hollow chamber or passage 17 leading to a threaded lower opening 18. A radially extending wall 19 is modified to form a mouthpiece member 20 adapted to be inserted between the lips 22 of a victim, and project to the area of the pharynx before the device is activated.

A curved elongate member 26 forms a tongue depressor, and includes an outer end 27, a short rectilinear portion 28, and a curved portion 29 adapted to overlie the tongue of the victim, and terminate in a free open end 30. A hollow passage 31 extends from the end 30 to the chamber 17.

The vacuum source element 11 is preferably in the form of a metal canister 35 having a cylindrical side wall 36 forming a manually engageable handle, a lower wall 37 and an upper wall 38. Although not essential for the practicing of the invention, the canister may be provided with bayonet interlocking means (not shown) to permit convenient replacement where required. As disclosed, the upper wall 38 includes a threaded opening 40 disposed beneath the valve means 13 for engaging the element 10.

The valves means 13 is preferably of a sliding piston type, and includes a valve body 41 having a vertical through bore 42. A piston 43 includes an area 44 of reduced diameter which, when aligned with a passage 45, allows the pressurized contents of the canister 35 to be discharged into a jet tube 46 at a nozzle 47 disposed within a tube 48 supporting and communicating with the element 11.

Upon the discovery of an emergency situation, the tongue depressor element 11 is inserted into the mouth of the patient as shown in FIG. 1 of the drawing sufficiently far to position the free end 30 in the area of the pharynx, where a large particle of food is positioned.

Once seated, the valve means 13 is actuated to permit a burst of suction to be applied from the end 30 to the large particle (not shown). During this procedure, the location of the free end may be shifted slightly until engagement of the particle is sensed. While still maintaining the suction, the device 10 is removed from the mouth of the victim, with the engaged particle. Should the particle be dislodged and fall free from the end of the tongue depressor element, it may be swallowed in normal fashion by the victim.

It will be observed that the device may be used by those possessed of only ordinary skill, with a minimum of training, unlike the use of surgical instruments normally used for this purpose. It is not necessary to seal the mouth and nostrils of the user during use, so that as soon as the particle is freed, the victim may resume normal breathing. During use of the device, no other manipulation of the patient is necessary, and the patient may remain either in a sitting or prone position.

We wish it to be understood that we do not consider the invention limited to the precise details of structure shown and set forth in this specification, for obvious modifications will occur to those skilled in the art to which the invention pertains.

We claim:

1. The method of removing obstructions lodged in the pharynx and/or larynx of a victim comprising the steps of:

providing a device including a tongue depressor element having a curved hollow member, a free end of which is insertable into the throat area of the victim, a source of compressed gas, a jet means for providing reduced atmospheric pressure at said free open end of said curved hollow member, and valving means for controlling operation of said jet means;

inserting said tongue depressor element into the mouth of a victim to a point where said free end of said curved hollow member is positioned in the area of the pharynx and/or larynx;

opening said valving means to cause suction at the free end of said tongue depressor element for a period of time sufficient to dislodge an obstruction and retain said obstruction on said free end; and while maintaining said reduced atmospheric pressure at said open end withdrawing said tongue depressor element through the mouth of the victim with an engaged obstruction.

* * * * *